(12) United States Patent
Hoeft

(10) Patent No.: US 6,640,129 B1
(45) Date of Patent: Oct. 28, 2003

(54) DETERMINATION OF LIVER FUNCTION USING THE RATE AT WHICH PLASMA DISAPPEARS

(76) Inventor: Andreas Hoeft, Neissestrasse 6, D-53127 Bonn (DE)

(*) Notice: Subject to any disclaimer, the term of this patent is extended or adjusted under 35 U.S.C. 154(b) by 0 days.

(21) Appl. No.: 09/486,670
(22) PCT Filed: Jul. 1, 1999
(86) PCT No.: PCT/DE99/01899
§ 371 (c)(1), (2), (4) Date: May 5, 2000
(87) PCT Pub. No.: WO00/01297
PCT Pub. Date: Jan. 13, 2000

(30) Foreign Application Priority Data

Jul. 1, 1998 (DE) .......................... 198 29 273

(51) Int. Cl.⁷ ................................. A61B 6/00
(52) U.S. Cl. .................. 600/431; 600/476; 600/479; 600/504; 424/9.6
(58) Field of Search .............. 424/9.4, 9.3, 9.6; 600/310, 473, 476, 479, 504, 431

(56) References Cited

U.S. PATENT DOCUMENTS 5,154,176 A * 10/1992 Kanda .................... 600/479
5,178,141 A * 1/1993 Kanda .................... 600/479
6,030,841 A * 2/2000 Mills ...................... 436/97

FOREIGN PATENT DOCUMENTS

| DE | 41 30 931 | 3/1993 |
| EP | 0 403 683 | 6/1989 |
| EP | 0 359 206 | 9/1989 |
| EP | 0 399 482 | 5/1990 |

* cited by examiner

Primary Examiner—Marvin M. Lateef
Assistant Examiner—Jeoyuh Lin
(74) Attorney, Agent, or Firm—Collard & Roe, P.C.

(57) ABSTRACT

A method and a device for determining liver function are described.

Liver function is determined after injection of an indicator dye into the bloodstream, optical measurement of the resulting concentration of indicator dye in the bloodstream and calculation of a plasma elimination rate from the dye concentration-time curve of the indicator dye.

An average circulation transit time $mtt_{circ}$ is calculated from the measurement of the dye concentration $c(t)$. In addition, a parameter k representing a fractional reentry rate of the indicator dye after each pass through the circulation is determined. The plasma elimination rate PER is calculated according to the equation:

$$PER = (1-k)/(k \cdot mtt_{circ}).$$

12 Claims, 2 Drawing Sheets

DETERMINATION OF LIVER FUNCTION USING THE RATE AT WHICH PLASMA DISAPPEARS

SUMMARY OF THE INVENTION

1. Field of the Invention

This invention concerns a method of determining liver function on the basis of a plasma elimination rate and a device for determining liver function on the basis of a plasma elimination rate.

2. The Prior Art

Liver function is an important parameter in intensive care medicine and plays a crucial role in determining the prognosis for extremely ill patients. At the present time, liver function is determined routinely in intensive care medicine on the basis of various laboratory parameters which characterize the synthesis performance and the elimination performance of the liver. However, the disadvantage of these laboratory values is that when liver function fails, these values do not become pathological until after a rather long latency period, so the liver dysfunction does not become evident for several days.

One possibility of evaluating liver function immediately, at least with regard to elimination performance, consists of administering indicator substances which are eliminated through the liver and determining the elimination time constant of these indicators. Indocyanine green is a common indicator used for this purpose. Indocyanine green is usually injected intravenously as a bolus, and then at least two blood samples, preferably several blood samples are taken at intervals of several minutes over a period of at least 15 minutes following the bolus injection. The elimination time constant can be calculated from the drop in indicator dye concentration in the blood specimens. However, this method is rarely used in clinical practice because it is still too time consuming because of the laboratory analyses.

SUMMARY OF THE INVENTION

The object of this invention is to create a method and a device with which liver function can be determined by non-invasively and the measurement result is available more rapidly.

The method and the device according to this invention measure a reduction in indicator concentration in the blood which occurs due to degradation of the indicator by the liver. After injecting a suitable indicator such as indocyanine green, into the bloodstream, a characteristic indicator concentration-time curve is obtained at a measurement point in the body when liver function is normal. First there is an initial maximum indicator concentration, and after a temporary decline, there is a second maximum indicator concentration. The second maximum occurs due to recirculation, i.e., a second pass is already occurring even before the concentration surge declines in the first pass.

An average circulation transit time $mtt_{circ}$ is calculated from the measurement of the curve of the indicator concentration over time c(t), and in addition, a parameter k representing a fractional recovery rate of the indicator dye after each pass through the circulation is also determined. Then with these values, the plasma elimination rate (PER) can be calculated according to the equation:

$$PER = (1-k)/(k \cdot mtt_{circ})$$

The result is available after only a few recirculation cycles.

The average circulation transit time $mtt_{circ}$ given above can be calculated from a circulation transport function g(t) which describes the transport behavior of the circulation. The average circulation transit time $mtt_{circ}$ is then obtained according to the equation:

$$mtt_{circ} = \frac{\int_0^\infty g(t) \cdot t \, dt}{\int_0^\infty g(t) \, dt}$$

The circulation transport function g(t) can be calculated from the measured indicator concentration with the help of an iterative nonlinear fitting method. In this method, with the stipulation of a model function:

$$g(t) = a_m g_m(t) + a_{m+1} g_{m+1}(t) + \ldots + a_n g_n(t)$$

with $$\sum_{m=1}^{n} am = 1,$$

where the individual compartments amgm are described by left-skewed distribution functions, a recursive convolution is performed according to the equations:

$$c(t) = c_{bolus}(t) + c_{rez}(t)$$

and $$c_{rez}(t) = k \cdot \int_0^t g(t-u) \cdot c(u) \, du$$

where the parameters k, $a_m$ and the parameters of the distribution functions are optimized by the method of the least squares deviation, with at least one compartment $a_1 g_1(t)$ being stipulated. In the equation, c(t) represents the concentration-time curve of the indicator dye, $c_{bolus}(t)$ represents the first portion of the indicator concentration-time curve fitting directly to the measurement site, $c_{rez}(t)$ denotes a recirculating portion of the indicator concentration-time curve and k denotes the elimination fraction of the indicator eliminated through the liver.

For a greater accuracy, two compartments ($a_1 g_1(t)$) and ($a_2 g_2(t)$) can be stipulated.

As an alternative, the optical measurement of the resulting indicator concentration in the bloodstream can be performed by fiber optic measurement in a central vessel or as a non-invasive method by measuring the light transmission or reflection of incident light at suitable body locations, in particular on the finger, earlobe, bridge of the nose, the forehead or the inside of the cheek (buccal mucosa).

BRIEF DESCRIPTION OF THE DRAWINGS

This invention is explained in greater detail below with reference to the drawing, which shows.

DETAILED DESCRIPTION OF THE PREFERRED EMBODIMENT

Figure 1:
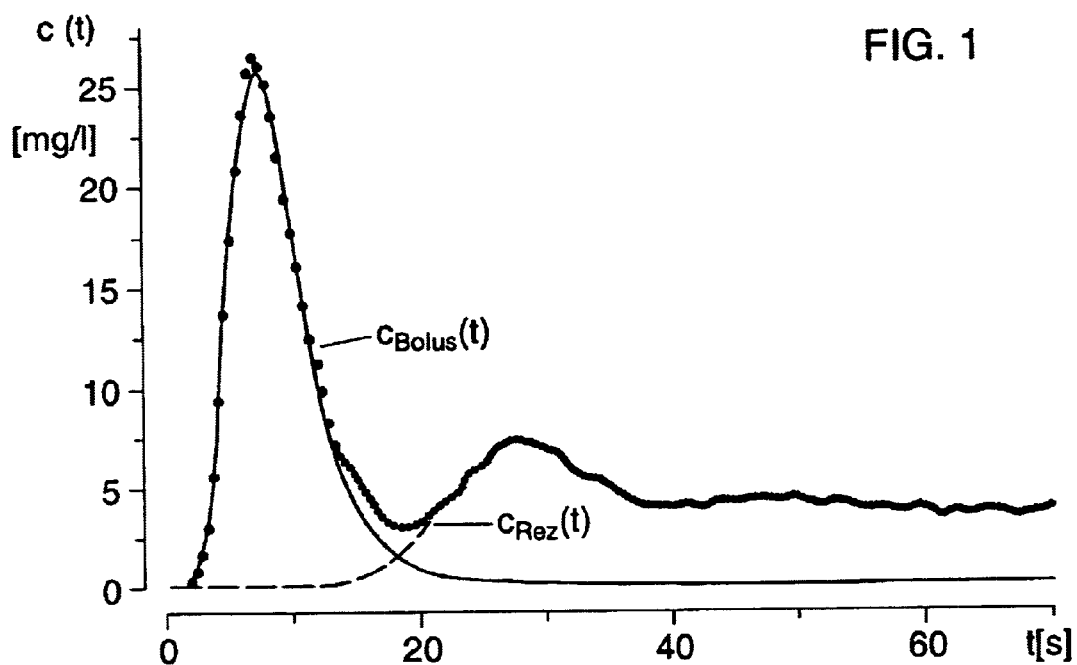
FIG. 1: a graphic plot of the concentration-time curve of an indicator dye.

FIG. 1 shows a graphic plot of the concentration-time curve of an indicator dye after a bolus injection. The second maximum following the first maximum occurs due to recirculation, i.e., a second pass occurs before the concentration surge subsides in a first pass.

Figure 4:
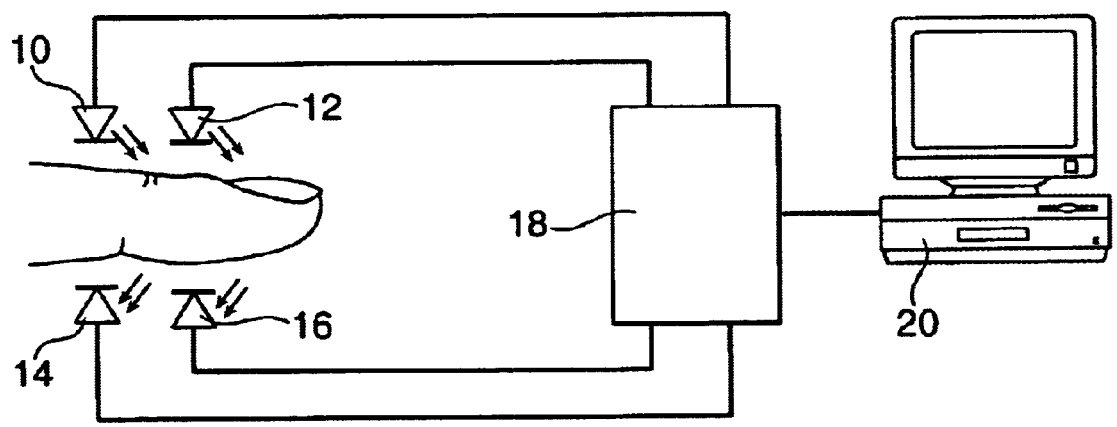
FIG. 4: a block diagram of a device for measuring and determining the plasma elimination rate.

Sensors connected to an analyzer circuit and a computer are arranged at a measurement point in the body to determine the indicator dye concentration-time curve. FIG. 4 shows an example of a device according to this invention. Two light transmitters 10 and 12 and two light receivers 14 and 16 are provided there and are connected to a computer 20 via an analyzer circuit 18. It shall be assumed that indocyanine green is used as the indicator dye for the measurement of liver function.

Use of a reference dye is advantageous but is not absolutely necessary. Hemoglobin, the red pigment in blood, may be used as the reference dye. In this case, the one light transmitter 10 operates at a wavelength of 800 nanometers (nm) and the other light transmitter 12 operates at a wavelength of 900 nanometers. The light receivers 14 and 16 may be designed to filter out these wavelengths preferentially. As an alternative, however, it is also possible to switch between two light transmitters 10 and 12, and in this case it is sufficient to have only one light receiver 14, but then it must be designed for both wavelengths.

The absorption properties of the dyes can be measured by measuring either the light transmission or the light reflection. Suitable sites on the body include the fingers, the earlobes, the bridge of the nose, the forehead or the inside of the cheek.

The light intensity signals received by light receivers 14 and 16 are analyzed by analyzer circuit 18 and sent to a computer 20. First the pulsatile components of the light intensities $I_{ind\,puls}(t)$ and $I_{ref\,puls}(t)$ are preprocessed in this computer 20, e.g., by forming the quotient:

$$I_{ind\,puls}(t) = I_{ind}(t-dt)/I_{ind}(t+dt)$$

$$I_{ref\,puls}(t) = I_{ref}(t-dt)/I_{ref}(t+dt)$$

In another step, the relative dye concentration can be determined as a function of time from these preprocessed signals, namely also by forming the quotient:

$$c(t) = I_{ind\,puls}/I_{ref\,puls}$$

No calibration factor is needed here, because only one linear signal is needed for the determination of the liver function. The measurement principle is not based on determination of absolute concentration values, but instead is based only on determination of time constants.

Then in further analysis of the dye concentration as a function of time, a circulation transport function g(t) describing the transport behavior of the circulation and a parameter k representing a functional reentry rate of the dye after each pass through the circulation are determined from c(t) by means of nonlinear fitting algorithms.

The following discussion is based on a model where a transport path of the injected indicator dye ICG as a bolus injection leads first through the lungs. Downstream from the lungs, the transport path is divided into a first rapid component, a second slow component and elimination of the dye through the liver. The first and second compartments then lead back to the lungs. The concentration of the indicator dye at the outlet of the lungs follows the function:

$$c(t) = c_{bolus}(t) + c_{rez}(t)$$

with $$c_{rez}(t) = k \cdot \int_0^t g(t-u) \cdot c(u)\,du$$

where c(t) represents the concentration-time curve of the indicator dye, $c_{bolus}(t)$ represents the first portion of the dye concentration-time curve fitting directly at the measurement site, $c_{rez}(t)$ represents a recirculating portion of the dye concentration-time curve, and k represents the fractional reentry rate of the dye after partial elimination through the liver. Therefore, the factor k is always smaller than 1.

The transport process is described by a convolution integral. Recirculation in this model means that the result of the convolution $c_{rez}(t)$ also influences the input function c(t) at the same time. Recirculation of the indicator thus leads to a relationship which is described in principle as follows:

$$c(t) = f[k, g(t), c(t)]$$

The compartments of the circulation model are stipulated for g(t). Preliminary studies have shown that one to two compartments can be stipulated for dye dilution curves measured on patients for g(t), depending on the desired accuracy. This yields the following result for the general model function:

$$g(t) = a_m g_m(t) + a_{m+1} g_{m+1}(t) + \ldots + a_n g_n(t)$$

with $$\sum_{m=1}^{n} am = 1$$

where the individual compartments $a_m g_m$ are described by left-skewed distribution functions. The specific equation for two compartments is:

$$g(t) = a_1 g_1(t) + a_2 g_2(t).$$

The circulation transport functions are calculated by computer from measured dye curves with the help of an iterative nonlinear fitting method, where with the stipulation of the model function:

$$g(t) = a_1 g_1(t) + a_2 g_2(t)$$

a recursive convolution is performed repeatedly according to the equations:

$$c(t) = c_{bolus}(t) + c_{rez}(t)$$

and $$c_{rez}(t) = k \cdot \int_0^t g(t-u) \cdot c(u)\,du$$

where k, $a_1$, $a_2$ and the parameters of the distribution functions are optimized by the method of the least squares deviation.

Figure 3:
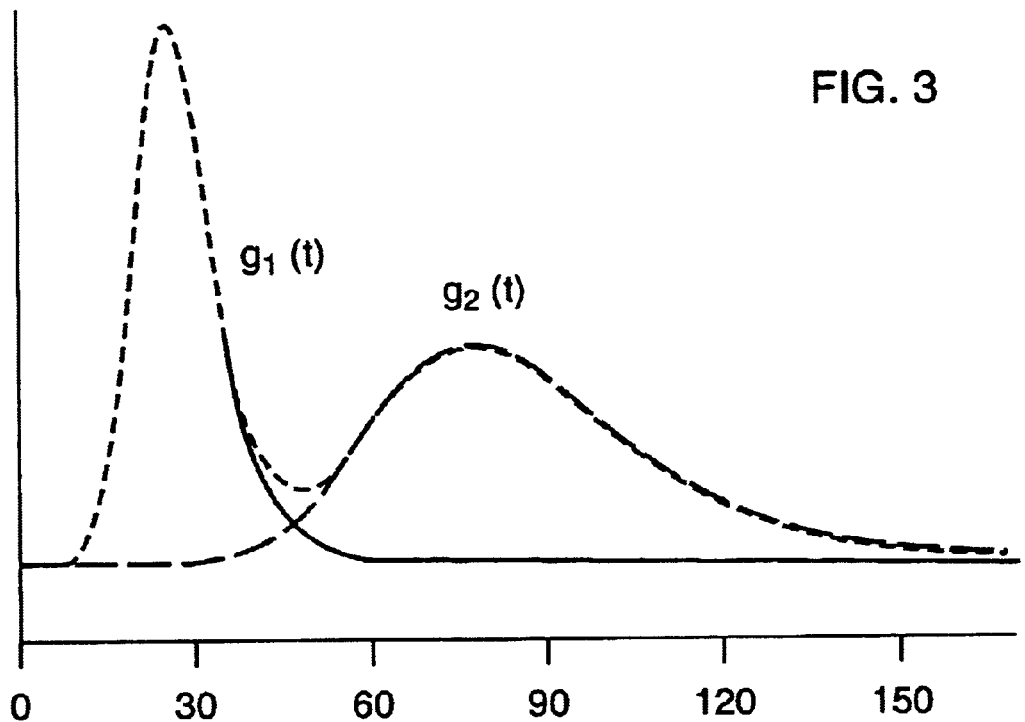

After performing these computation steps, this yields a transport function such as that calculated as an example for the data for two compartments as obtained in FIG. 1 and as plotted in FIG. 3. The resulting transport function g(t) is composed of the transport function g1(t) for the first compartment and g2(t) for the second compartment. In addition, the average circulation transit time ($mtt_{circ}$) which is the first moment of g(t), is calculated from the transport function g(t):

$$mtt_{circ} = \frac{\int_0^\infty g(t) \cdot t \, dt}{\int_0^\infty g(t) \, dt}$$

The plasma elimination rate (PER) of the indicator dye indocyanine green is then obtained as follows:

$$PER = (1-k)/(k \cdot mtt_{circ}).$$

Figure 2:
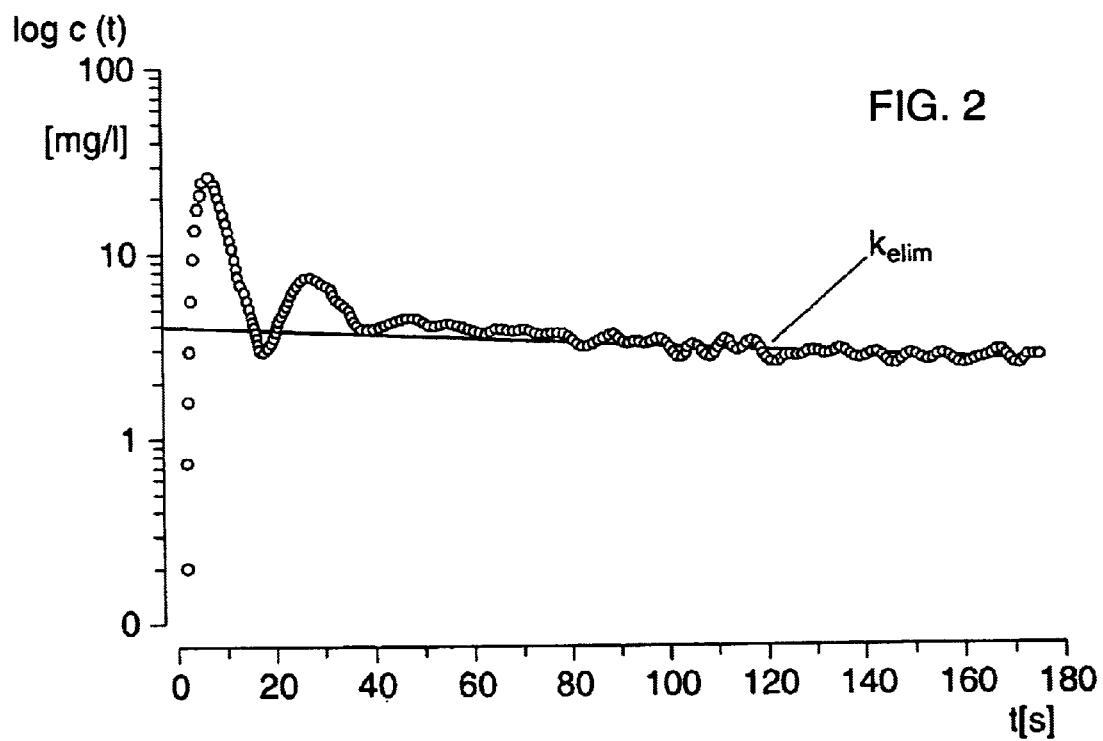
FIG. 2: a semilogarithmic plot of the concentration-time curve according to FIG. 1, FIG. 3: a graphic plot of the circulation transport function.

An alternative method would be to determine the time constant $K_{elim}$ of the elimination phase in the linear portion of the curve in the semilogarithmic plot of the concentration-time curve according to FIG. 2. In this case, the plasma elimination rate (PER) is:

$$PER = K_{elim}/\cdot 100 \cdot 60 \text{(for conversion to units /\%/m)}.$$

What is claimed is:

1. A method of determining liver function of a patient having a circulation on the basis of plasma elimination rate (PER), comprising the steps of:
   (a) injecting an indicator dye into a bloodstream of said patient;
   (b) performing an optical measurement of a resulting concentration of indicator dye in the bloodstream;
   (c) calculating the plasma elimination rate (PER) from a dye concentration-time curve of the indicator dye; wherein calculating the plasma elimination rate (PER) includes:
      (i) calculating an average circulation transit time ($mtt_{circ}$) from the measurement of the dye concentration (c(t));
      (ii) determining a parameter (k) representing a fractional reentry rate of the indicator dye after each pass through the circulation; and
      (iii) calculating the plasma elimination rate (PER) according to the equation $$PER = (1-k)/(k \cdot mtt_{circ}).$$

2. A method according to claim 1, wherein calculating the average circulation transit time ($mtt_{circ}$) is performed according to the equation $$mtt_{circ} = \frac{\int_0^\infty g(t) \cdot t \, dt}{\int_0^\infty g(t) \, dt}$$

wherein g(t) is a circulation transport function which describes a transport behavior of the circulation.

3. A method according to claim 2, wherein the circulation transport function g(t) is calculated from the measured dye concentration employing an iterative nonlinear fitting method which includes performing repeatedly a recursive convolution according to the equations $$c(t) = c_{bolus}(t) + c_{rez}(t)$$

and $$c_{rez}(t) = k \cdot \int_0^t g(t-u) \cdot c(u) \, du$$

wherein
   c(t) represents the concentration-time curve of the indicator dye,
   $c_{bolus}(t)$ represents a first fraction of the dye concentration-time curve directly at the measurement site,
   $c_{rez}(t)$ represents a recirculating fraction of the dye concentration-time curve,
   k represents a fractional reentry rate of the dye due to elimination through the liver,
and wherein a model function $$g(t) = a_m g_m(t) + a_{m+1} g_{m+1}(t) + \ldots + a_n g_n(t)$$

with $$\sum_{m=1}^n a_m = 1$$

is stipulated with individual compartments, $a_m g_m$ being described by left-skewed distribution functions and at least one compartment $a_1 g_1(t)$ being stipulated,
   wherein k and $a_m$ and parameters of distribution functions are optimized according to a least square deviation method.

4. A method according to claim 3, wherein two compartments $a_1 g_1(t) + a_2 g_2(t)$ are stipulated.

5. A method according to claim 1, wherein the optical measurement of the resulting dye concentration in the bloodstream is performed by means of a fiber optic measurement in a central vessel.

6. A method according to claim 1, wherein the optical measurement of the resulting dye concentration in the bloodstream is performed by measuring one of the group of:
   light transmission and
   reflection of incident light in a non-invasive way at a suitable location on the body comprising a finger, earlobe, bridge of nose, buccal mucosa or forehead.

7. A device for determining liver function of a patient having a circulation on the basis of plasma elimination rate (PER), comprising:
   (a) an optical measurement sensor for determining an indicator dye concentration in a bloodstream of the patient resulting from an injection of indicator dye into the bloodstream; and
   (b) a computer for determining the plasma elimination rate (PER) from a dye concentration-time curve of the indicator dye,
   wherein the computer is controlled such that an average circulation transit time ($mtt_{circ}$) is calculated from the measurement of the dye concentration (c(t)); a parameter (k) representing a fractional reentry rate of the indicator dye after each pass through the circulation is determined, and the plasma elimination rate (PER) is calculated according to the equation $$PER = (1-k)/(k \cdot mtt_{circ}).$$

8. A device according to claim 7, wherein the computer is controlled such that calculating the average circulation transit time ($mtt_{circ}$) is performed according to the equation $$mtt_{circ} = \frac{\int_0^\infty g(t) \cdot t \, dt}{\int_0^\infty g(t) \, dt}$$

wherein g(t) is a circulation transport function which describes transport behavior of the circulation.

9. A device according to claim 8, wherein the computer is controlled such that the circulation transport function g(t) is calculated from the measured dye concentration employing an iterative nonlinear fitting method which includes performing repeatedly a recursive convolution according to the equations $$c(t) = c_{bolus}(t) + c_{rez}(t)$$

and $$c_{rez}(t) = k \cdot \int_0^t g(t-u) \cdot c(u) \, du$$

wherein c(t) represents the concentration-time curve of the indicator dye, $c_{bolus}(t)$ represents a first fraction of the dye concentration-time curve directly at the measurement site $c_{rez}(t)$ represents a recirculating fraction of the dye concentration-time curve k represents a fractional reentry rate of the dye due to elimination through the liver and wherein a model function $$g(t) = a_m g_m(t) + a_{m+1} g_{m+1}(t) + \ldots + a_n g_n(t)$$

with $$\sum_{m=1}^n a_m = 1$$

is stipulated with individual compartments, $a_m g_m$ being described by left-skewed distribution functions and at least one compartment $a_1 g_1(t)$ being stipulated, wherein k and $a_m$ and parameters of distribution functions are optimized according to a least square deviation method.

10. A device according to claim 9, wherein the computer is controlled such that two compartments $a_1 g_1(t) + a_2 g_2(t)$ are stipulated.

11. A device according to claim 7, wherein the optical measurement sensor is a fiberoptic catheter adapted for being arranged in a central vessel for performing the measurement.

12. A device according to claim 7, wherein the optical measurement sensor includes:
a light transmitter and
a light receiver,
both of said light transmitter and light receiver being adapted to measure one of the group of:
light transmission and
reflection of incident light in a non-invasive way at a suitable location on the body comprising a finger, earlobe, bridge of nose, inside of cheek or forehead.

* * * * *